May 18, 1965 F. W. ANDERSON Plant Pat. 2,515
APRICOT TREE
Filed Feb. 28, 1964
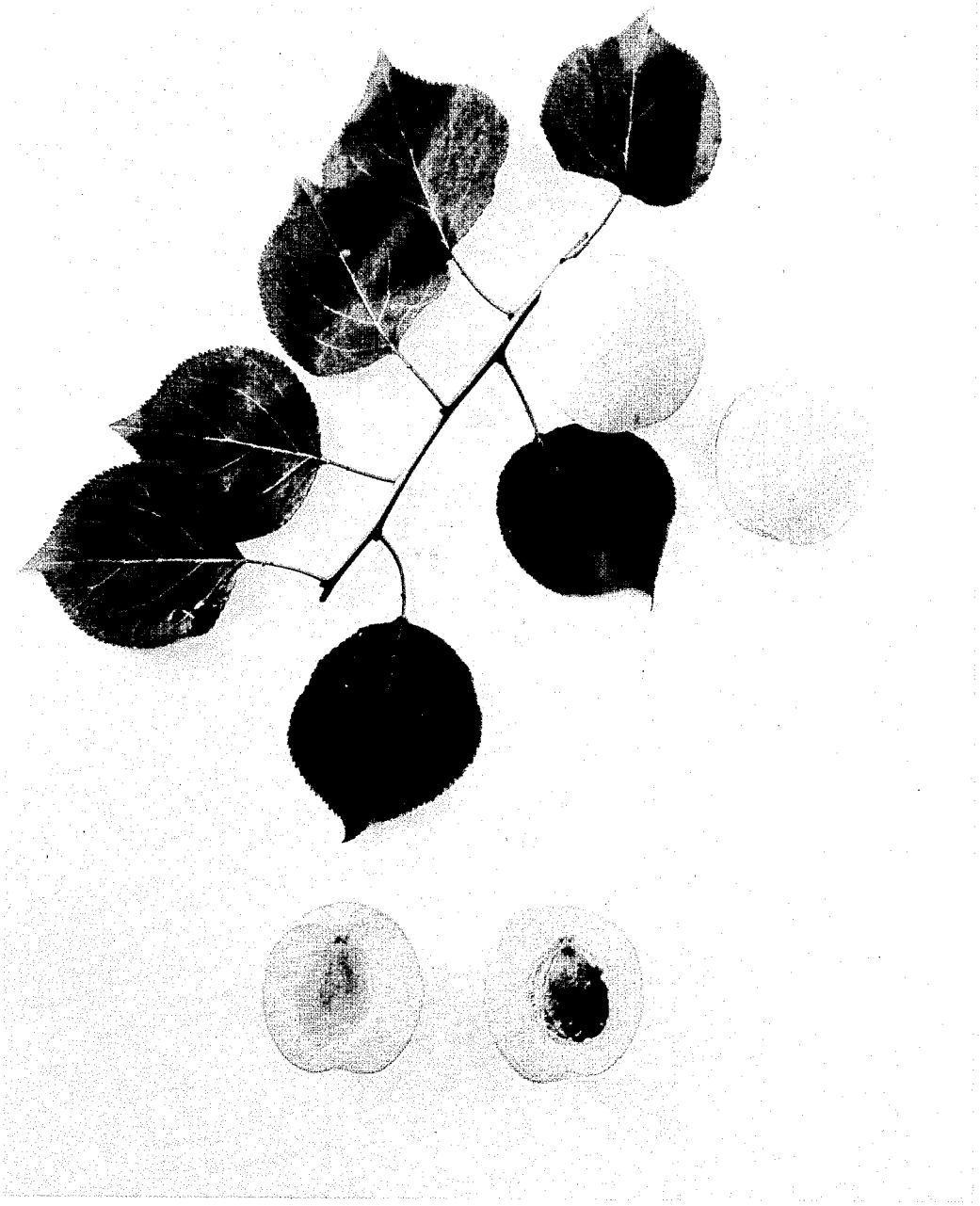
INVENTOR
Frederic W. Anderson
Webster & Webster
ATTYS.

United States Patent Office

Plant Pat. 2,515
Patented May 18, 1965

2,515
APRICOT TREE

Frederic W. Anderson, Merced, Calif., assignor to Kim Bros., doing business as Reedley Nursery, Reedley, Calif., a copartnership Filed Feb. 28, 1964, Ser. No. 348,310
1 Claim. (Cl. Plt.—39)

This invention relates to a new and distinct variety of apricot tree.

The variety was originated by me, during a long and continuing plant breeding program seeking improved fruit varieties, as a selected second generation seedling of the Perfection (unpatented). Such origination of the variety was accomplished by me under conditions of careful observation in my experimental orchard located near Le Grand, county of Merced, State of California.

Subsequent to origination of the variety, and the recognition by me of its novel characteristics as later described, I asexually reproduced the variety by top-working on mature fruit trees in my experimental orchard located as aforesaid. In maturity, all of such asexual reproductions ran true to the parent tree in all respects.

The present variety of apricot tree is distinctively characterized, and advantageous for commercial growing, in the following respects:

The fruit of the instant variety ripens and is in harvest earlier than any other variety now grown for a commercial crop. The harvest period approximates one week earlier than Newcastle, Derby, and Pomo, two weeks earlier than Perfection, three weeks earlier than Blenheim, and a month earlier than the Tilton.

All of the above mentioned previously existing varieties are unpatented except Pomo (United States Plant Patent No. 2,192).

Further, the fruit of the present variety, in addition to early ripening, has quite firm flesh and remains in good marketable condition for a remarkably long time, both on the tree and after picking.

The drawing comprises an illustration, by photographic reproduction in color, of the fruit and leaves at harvest time; one fruit being shown as cut in half to expose the flesh, and with the stone remaining in place in one half.

Referring now more specifically to the pomological details of this new and distinct variety of apricot tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Spreading.
- *Density.*—Open.
- *Production.*—Very productive.
- *Bearing.*—Regular bearer.

Trunk:
- *Form.*—Medium.
- *Texture.*—Medium.

Branches:
- *Form.*—Medium.
- *Texture.*—Medium.
- *Lenticels.*—Size—medium.

Leaves:
- *Size.*—Medium. Average length—3⅛". Average width—3".
- *Form.*—Cordate; acutely pointed.
- *Thickness.*—Thick.
- *Texture.*—Smooth.
- *Margin.*—Crenate.
- *Petiole.*—Medium length.
- *Glands.*—Average number and position—1 to 3 on petiole and 2 on blade. Alternate; small.
- *Color.*—Top side—Medium Green (22–L–8). Under side—Lighter Green (21–F–7).

Flower buds: Size—medium.

Flowers:
- *Date of first bloom.*—February 27, 1963.
- *Date of full bloom.*—March 8, 1963.
- *Size.*—Medium.
- *Color.*—White.

Fruit:
- *Maturity when described.*—Eating ripe.
- *Dates of first and last picking.*—May 28, 1963, and June 10, 1963, respectively.
- *Size.*—Small to medium. Average diameter axially—1⅞". Average transversely in suture plane—1⅞".
- *Form.*—Uniform; symmetrical; globose to slightly oblong.
- *Suture.*—An inconspicuous line. Shallow, extends from base to apex.
- *Ventral surface.*—Rounded strongly.
- *Cavity.*—Rounded. Average depth—¼". Average breadth—⅝".
- *Apex.*—Depressed.

Skin:
- *Tendency to crack.*—Very slight.
- *Down.*—Scant; short.
- *Color.*—Normal apricot (10–L–8).

Flesh:
- *Amygdalin.*—Wanting.
- *Juice.*—Moderate.
- *Texture.*—Firm; meaty.
- *Fibers.*—Few.
- *Ripens.*—Evenly.
- *Flavor.*—Acid to subacid.
- *Aroma.*—Wanting.
- *Eating quality.*—Fair to good.
- *Color.*—Normal apricot (9–L–7).

Stone:
- *Type.*—Free.
- *Size.*—Small to medium. Average length—1". Average breadth—15/16". Average thickness—9/16".
- *Form.*—Globose.
- *Base.*—Straight.
- *Apex.*—Rounded.
- *Sides.*—Equal.
- *Ventral edge.*—Thin, without wing toward base.
- *Dorsal edge.*—Narrow, with shallow groove throughout.
- *Ridges.*—Interrupted.
- *Tendency to split.*—None.
- *Color.*—Brown (8–H–8).

Use: Dessert; long distance shipping; drying; freezing; canning.

Keeping quality: Excellent.

Shipping quality: Excellent.

The apricot tree and its fruit herein described may vary in slight detail due to climatic and soil conditions under which the variety may be grown; the present description being of the variety as grown in the Central Valley of California.

The following is claimed:

A new and distinct variety of apricot tree, as illustrated and described, which is a regular and very productive bearer of small to medium size, globose to slightly oblong fruit having excellent shipping and keeping qualities; said variety being particularly characterized as to novelty, by early ripening fruit having firm flesh which remains in good marketable condition for a relatively long time both on the tree and after picking; such fruit ripening about one week earlier than the Newcastle, Derby, and Pomo.

No references cited.

ABRAHAM G. STONE, *Primary Examiner.*